(12) United States Patent
Johnson et al.

(10) Patent No.: US 9,974,594 B2
(45) Date of Patent: May 22, 2018

(54) SYSTEM AND METHOD FOR SENSING TISSUE CHARACTERISTICS

(71) Applicant: COVIDIEN LP, Mansfield, MA (US)

(72) Inventors: Kristin D. Johnson, Louisville, CO (US); Kyle R. Rick, Boulder, CO (US); Christopher A. Valentine, Boulder, CO (US); Mika N. Sinanan, Brier, WA (US)

(73) Assignee: COVIDIEN LP, Mansfield, MA (US)

( * ) Notice: Subject to any disclaimer, the term of this patent is extended or adjusted under 35 U.S.C. 154(b) by 941 days.

(21) Appl. No.: 14/467,914

(22) Filed: Aug. 25, 2014

(65) Prior Publication Data
US 2014/0364849 A1 Dec. 11, 2014

Related U.S. Application Data

(62) Division of application No. 12/791,100, filed on Jun. 1, 2010, now Pat. No. 8,834,462.

(51) Int. Cl.
*A61B 18/18* (2006.01)
*A61B 18/04* (2006.01)
*A61B 18/00* (2006.01)

(52) U.S. Cl.
CPC .. *A61B 18/042* (2013.01); *A61B 2018/00166* (2013.01); *A61B 2018/00577* (2013.01);
(Continued)

(58) Field of Classification Search
CPC ........ A61B 18/042; A61B 2018/00166; A61B 2018/00577; A61B 2018/00642;
(Continued)

(56) References Cited

U.S. PATENT DOCUMENTS 3,434,476 A 3/1969 Shaw et al.
3,671,195 A 6/1972 Bersin
(Continued)

FOREIGN PATENT DOCUMENTS

CN 2391565 Y 8/2000
DE 3710489 A1 11/1987
(Continued)

OTHER PUBLICATIONS

Supplementary European Search Report from Appl. No. EP 09 75 5799 completed dated Aug. 31, 2012.
(Continued)

*Primary Examiner* — Michael Peffley
*Assistant Examiner* — Amanda Zink

(57) ABSTRACT

A medical device for treating and analyzing tissue includes a plasma applicator having a housing. The housing includes a substantially tubular shape and defines a lumen therethrough. The lumen is in fluid communication with an ionizable media source configured to supply ionizable media thereto. The applicator also includes one or more electrodes coupled to the housing. The electrodes are adapted to couple to a power source configured to energize the electrodes to ignite the ionizable media to form a plasma plume for treating tissue. The device also includes an effluent-collection attachment coupled to the plasma applicator. The effluent-collection attachment is configured to collect a portion of a plasma effluent.

13 Claims, 4 Drawing Sheets

(52) U.S. Cl.
CPC ............ *A61B 2018/00642* (2013.01); *A61B 2018/00755* (2013.01); *A61B 2018/00875* (2013.01); *A61B 2018/00922* (2013.01); *A61B 2218/008* (2013.01)

(58) Field of Classification Search
CPC .......... A61B 2018/00755; A61B 2018/00875; A61B 2018/00922; A61B 2218/008
See application file for complete search history.

(56) References Cited

U.S. PATENT DOCUMENTS

| | | | |
|---|---|---|---|
| 3,903,891 | A | 9/1975 | Brayshaw |
| 4,781,175 | A | 11/1988 | McGreevy et al. |
| 5,088,997 | A | 2/1992 | Delahuerga et al. |
| 5,217,457 | A | 6/1993 | Delahuerga et al. |
| 5,656,186 | A | 8/1997 | Mourou et al. |
| 5,836,944 | A | 11/1998 | Cosmescu |
| 6,033,582 | A | 3/2000 | Lee et al. |
| 6,099,523 | A | 8/2000 | Kim et al. |
| 6,149,620 | A | 11/2000 | Baker et al. |
| 6,149,648 | A | 11/2000 | Cosmescu |
| 6,159,531 | A | 12/2000 | Dang et al. |
| 6,172,130 | B1 | 1/2001 | Bellesort |
| 6,264,650 | B1 | 7/2001 | Hovda et al. |
| 6,464,889 | B1 | 10/2002 | Lee et al. |
| 6,565,558 | B1 | 5/2003 | Lindenmeier et al. |
| 6,861,377 | B1 | 3/2005 | Hirai et al. |
| 6,890,332 | B2 | 5/2005 | Truckai et al. |
| 6,958,063 | B1 | 10/2005 | Soll et al. |
| 7,165,451 | B1 | 1/2007 | Brooks et al. |
| 7,316,682 | B2 * | 1/2008 | Konesky ............. A61B 18/042 606/40 |
| 7,382,129 | B2 | 6/2008 | Mills |
| 7,445,619 | B2 | 11/2008 | Auge, II et al. |
| 7,497,119 | B2 | 3/2009 | Brooks et al. |
| 7,608,839 | B2 | 10/2009 | Coulombe et al. |
| 7,824,870 | B2 | 11/2010 | Kovalcheck et al. |
| 8,057,468 | B2 | 11/2011 | Konesky |
| 8,834,462 | B2 | 9/2014 | Johnson et al. |
| 2001/0025177 | A1 | 9/2001 | Woloszko et al. |
| 2002/0022836 | A1 | 2/2002 | Goble et al. |
| 2002/0045811 | A1 | 4/2002 | Kittrell et al. |
| 2003/0008327 | A1 | 1/2003 | Ornatskaia |
| 2003/0027186 | A1 | 2/2003 | Pierce |
| 2003/0208194 | A1 | 11/2003 | Hovda et al. |
| 2004/0027127 | A1 | 2/2004 | Mills |
| 2004/0111219 | A1 | 6/2004 | Gulati |
| 2004/0116918 | A1 * | 6/2004 | Konesky ............. A61B 18/042 606/34 |
| 2005/0015001 | A1 | 1/2005 | Lec et al. |
| 2006/0127879 | A1 | 6/2006 | Fuccione |
| 2006/0172429 | A1 | 8/2006 | Nilsson et al. |
| 2006/0224146 | A1 | 10/2006 | Lin |
| 2007/0014752 | A1 | 1/2007 | Roy et al. |
| 2007/0039389 | A1 | 2/2007 | Brooks et al. |
| 2007/0213704 | A1 | 9/2007 | Truckai et al. |
| 2007/0258329 | A1 | 11/2007 | Winey |
| 2007/0292972 | A1 | 12/2007 | Paulussen et al. |
| 2008/0125772 | A1 | 5/2008 | Stone et al. |
| 2008/0167398 | A1 | 7/2008 | Patil et al. |
| 2009/0281536 | A1 | 11/2009 | Beckman et al. |
| 2010/0082019 | A1 | 4/2010 | Neev |
| 2010/0331911 | A1 | 12/2010 | Kovalcheck et al. |
| 2011/0077642 | A1 | 3/2011 | Farin |
| 2012/0283732 | A1 * | 11/2012 | Lam ................. A61B 17/00491 606/49 |
| 2012/0289954 | A1 * | 11/2012 | Lam ................... A61B 17/3207 606/33 |
| 2014/0074090 | A1 * | 3/2014 | Lam ..................... A61B 18/042 606/49 |

FOREIGN PATENT DOCUMENTS

| | | |
|---|---|---|
| DE | 4139029 A1 | 6/1993 |
| DE | 4326037 A1 | 2/1995 |
| DE | 9117019 U1 | 3/1995 |
| DE | 19524645 A1 | 2/1997 |
| DE | 19537897 A1 | 3/1997 |
| DE | 9117299 U1 | 3/2000 |
| DE | 19848784 A1 | 5/2000 |
| DE | 29724247 U1 | 8/2000 |
| EP | 0956827 A1 | 11/1999 |
| FR | 1340509 A | 10/1963 |
| GB | 2458329 A | 9/2009 |
| JP | 61-159953 A | 7/1986 |
| SU | 1438745 A1 | 11/1988 |
| WO | 2009/080273 A1 | 7/2009 |
| WO | 2009/146432 A1 | 12/2009 |
| WO | 2009146439 A1 | 12/2009 |
| WO | 2010004403 A1 | 1/2010 |

OTHER PUBLICATIONS

Examiner's First Report issued in corresponding Australian Application No. 2011202512 dated Aug. 8, 2011.
U.S. Appl. No. 08/383,162, filed Feb. 3, 1995.
U.S. Appl. No. 08/619,380, filed Mar. 21, 1996.
U.S. Appl. No. 08/621,151, filed Mar. 21, 1996.
U.S. Appl. No. 08/878,694, filed Jun. 19, 1997.
U.S. Appl. No. 09/270,856, filed Mar. 17, 1999.
U.S. Appl. No. 09/504,640, filed Feb. 16, 2000.
U.S. Appl. No. 09/666,312, filed Sep. 21, 2000.
U.S. Appl. No. 12/606,672, filed Sep. 30, 2009.
U.S. Appl. No. 12/791,100, filed Jun. 1, 2010.
U.S. Appl. No. 12/845,842, filed Jul. 29, 2010.
Hernandez et al., "A Controlled Study of the Argon Beam Coagultor for Partial Nephrectomy"; The Journal of Urology, vol. 143, May 1990 J. Urol. 143: pp. 1062-1065.
Ward et al., "A Significant New Contribution to Radical Head and Neck Surgery"; Arch Otolaryngology, Head and Neck Surg., vol. 115 pp. 921-923 (Aug. 1989).
Moore et al., "Confined Geometry Interactions of Downstream RF-Excited Atmospheric Plasma Wires", IEEE Transactions on Plasma Science, 0093-3813, (2008) pp. 1-2.
Walsh et al., "Contrasting Characteristics of Pulsed and Sinusoidal Cold Atmospheric Plasma Jets", Applied Physics Letters, 88, 171501 (2006) pp. 1-3.
Cho et al., "Coplanar ac Discharges Between Cylindrical Electrodes With a Nanoporous Alumina Dielectric: Modular Dielectric Barrier Plasma Devices", IEEE Transactions on Plasma Science, vol. 33, No. 2, (Apr. 2005) pp. 378-379.
Xu et al., "DBD Plasma Jet in Atmospheric Pressure Argon", IEEE Transactions on Plasma Science, vol. 36, No. 4, (Aug. 2008), pp. 1352-1353.
Brand et al., "Electrosurgical Debulking of Ovarian Cancer: A New Technique Using the Argon Beam Coagulator"; Gynecologic Oncology 39 pp. 115-118 (1990).
Grund et al., "Endoscopic Argon Plasma . . . Flexible Endoscopy"; Endoscopic Surgery and Allied Technologies, No. 1, vol. 2, pp. 42-46 (Feb. 1994).
Waye et al., "Endoscopic Treatment Options"; Techniques in Therapeutic Endoscopy, pp. 1.7-1.15, (1987).
B.D. Cullity, "Introduction to Magnetic Materials", University of Notre Dame; Addison-Wesley Publishing Company, Reading MA., (1972) pp. 23-28.
Yin et al., "Miniaturization of Inductively Coupled Plasma Sources", IEEE Transactions on Plasma Science, vol. 27, No. 5, (Oct. 1999) pp. 1516-1524.
Park et al., "Nanoporous Anodic Alumina Film on Glass: Improving Transparency by an Ion-Drift Process", Electrochemical and Solid-State Letters, 8 (3) (2005), pp. D5-D7.
Cho et al., "Ozone Production by Nanoporous Dielectric Barrier Glow Discharge in Atmospheric Pressure Air", Applied Physics Letters, 92, 101504, (2008) pp. 1-3.

(56) References Cited

OTHER PUBLICATIONS

Akitsu et al., "Plasma Sterilization Using Glow Discharge at Atmospheric Pressure", Surface & Coatings Technology 193, (2005) pp. 29-34.
Koo et al., "Room-temperature Slot Microplasma in Atmospheric Pressure Air Between Cylindrical Electrodes With a Nanoporous Alumina Dielectric", Applied Physics Letters, 91, 041502 (2007) pp. 1-3.
Farin et al., Technology of Argon Plasma . . . Endoscopic Applications; Endoscopic Surgery and Allied Technologies, No. 1, vol. 2, pp. 71-77 (Feb. 1994).
Gupta et al., "The Potential of Pulsed Underwater Streamer Discharges as a Disinfection Technique", IEEE Transactions on Plasma Science, vol. 36, No. 4, (Aug. 2008) pp. 1621-1632.
Mark H. Mellow, "The Role of Endoscopic Laser Therapy in Gastrointestinal Neoplasms"; Advanced Therapeutic Endoscopy, pp. 17-21, (1990).
Silverstein et al., "Thermal Coagulation Therapy for Upper Gastrointestinal Bleeding"; Advanced Therapeutic Endoscopy, pp. 79-84, 1990.
European Search Report EP 01 10 2843.8, dated May 15, 2001.
European Search Report EP 05 00 2257, dated Jun. 1, 2005.
European Search Report EP 06 01 9572 dated Nov. 21, 2006.
European Search Report EP 07 00 4356 dated Jul. 2, 2007.
European Search Report EP 07 00 4659 dated Feb. 19, 2008.
European Search Report EP 07 00 4659—partial dated May 24, 2007.
European Search Report EP 09 00 4975 dated Sep. 11, 2009.
European Search Report EP 09 01 0519 dated Nov. 16, 2009.
European Search Report EP 09 01 0520 dated Dec. 10, 2009.
European Search Report EP 09 01 5212.5 dated Apr. 1, 2010.
European Search Report EP 09 17 1599.5 dated Mar. 16, 2010.
European Search Report EP 09 17 1600.1 dated Jan. 26, 2010.
International Search Report PCT/US98/19284, dated Jan. 14, 1999.
European Search Report for European Application No. 11168420.5 dated Dec. 22, 2011.
Extended European Search Report issued in Appl. No. 10849146.5 dated Sep. 9, 2013.
Schafer, et al. "In Vivo, in Situ Tissue Analysis Using Rapid Evaporative Ionization Mass Spectrometry," Angew. Chem. Int. Ed. 2009, 48, pp. 8240-8242.
Juan Fernandez de la Mora, "Real-time Detection of Human Skin Vapours," http://www.growthconsulting.frost.com/web/images.nsf/0/22475022D91FC05A65- 2576390033F777/$File/MI%20Oct09%20TIalert.htm; 1 page.

* cited by examiner

SYSTEM AND METHOD FOR SENSING TISSUE CHARACTERISTICS

CROSS-REFERENCE TO RELATED APPLICATIONS

This application is a Divisional Application of U.S. patent application Ser. No. 12/791,100, filed on Jun. 1, 2010, the entire contents of which are incorporated by reference herein.

BACKGROUND

Technical Field

The present disclosure relates to plasma applicators and processes for surface processing and material removal. More particularly, the disclosure relates to an apparatus and method for generating and directing plasma-generated species in a plasma applicator for removing and analyzing tissue.

Background of Related Art

Electrical discharges in dense media, such as liquids and gases at or near atmospheric pressure, can, under appropriate conditions, result in plasma formation. Plasmas have the unique ability to create large amounts of chemical species, such as ions, radicals, electrons, excited-state (e.g., metastable) species, molecular fragments, photons, and the like. The plasma species may be generated in a variety of internal energy states or external kinetic energy distributions by tailoring plasma electron temperature and electron density. In addition, adjusting spatial, temporal and temperature properties of the plasma creates specific changes to the material being irradiated by the plasma species and associated photon fluxes. Plasmas are also capable of generating photons including energetic ultraviolet photons that have sufficient energy to initiate photochemical and photocatalytic reaction paths in biological and other materials that are irradiated by the plasma photons.

SUMMARY

Plasma has broad applicability to provide alternative solutions to industrial, scientific and medical needs, especially workpiece surface processing at low temperature. Plasmas may be delivered to a workpiece, thereby affecting multiple changes in the properties of materials upon which the plasmas impinge. Plasmas have the unique ability to create large fluxes of radiation (e.g., ultraviolet), ions, photons, electrons and other excited-state (e.g., metastable) species which are suitable for performing material property changes with high spatial, material selectivity, and temporal control. The plasma may remove a distinct upper layer of a workpiece but have little or no effect on a separate underlayer of the workpiece or it may be used to selectively remove a particular tissue from a mixed tissue region or selectively remove a tissue with minimal effect to adjacent organs of different tissue type.

The present disclosure provides for systems and methods for removing and analyzing tissue using plasma and other energy-based devices. During application of plasma, tissue component molecules are vaporized and form an effluent that may then be collected and analyzed either subsequently or in real-time to identify types of tissue. This is particularly useful in cancer treatment procedures where real-time or rapid determination between malignant and normal tissues is beneficial in determining safe treatment margins.

In one embodiment, laser-induced breakdown spectroscopy ("LIBS") may be utilized in combination with a laser-based tissue treatment device. LIBS uses a pulsed laser in conjunction with one or more focusing lenses to create a spark on the surface of the tissue. The resulting optical emission produced by the spark is then analyzed by a spectrometer system. In particular, LIBS excites electrons via a laser, and the electron decay is then detected in an optical spectrometer. In another embodiment, mass spectrometry may be utilized. Prior to analysis, the sample is ionized, for example, via a high voltage electrode, and the ions are then accelerated in an electric field to a detector.

In a further embodiment, a plasma-based system may be combined with a spectrometer system to provide for more rapid tissue removal as well as generating identifiable molecules in the effluent for analysis. A plasma system according to the present disclosure includes a power source and an ionizable media source coupled to plasma applicator that initiates and maintains a plasma plume. The plasma applicator supplies the plasma plume to the tissue and includes one or more effluent-collection attachments for collecting vaporized gas and/or particles released by the tissue upon application of plasma thereto. The plasma system further includes a spectrometer that evaluates and identifies the constituents of the tissue and outputs that information to the user. The plasma system supplies excited atoms and/or pre-ionized molecules to the spectrometer, eliminating the need for a secondary ionization source in the spectrometer. The plasma system serves a dual purpose as a treatment device and as an excitation source for supplying ions and molecules to a spectrometer. The information from the spectrometer may be outputted in a variety of formats, e.g., identifying ratio of malignant vs. normal tissue, listing percentages of specific compounds, etc. Based on the displayed information, the user can determine progression of the tissue removal procedure and decide whether adequate treatment margins have been reached.

The effluent-collection attachment may be an evacuation tube coupled to the plasma applicator. The tube includes one or more filters for catching molecules from the effluent. The filters may be of various sizes to sort the particles based on their size. The molecules may then be evaluated by removing the filters and evaluating the molecules using any suitable spectroscopy systems such as LIBS, spark-induced breakdown spectroscopy, bio-aerosol mass spectrometry, and the like. In another embodiment, the effluent-collection attachment may be a secondary plasma chamber that further breaks down the plasma effluent emanating from the tissue. In addition to monitoring the size and type of particles of the plasma effluent, the system may also monitor for spikes in secondary or other harmonics, which are associated with different types of tissue being removed.

In another embodiment, the tissue may be treated with a contrast agent or marker that is delivered into tissue, either locally or systemically. The contrast agent may be any compound that is absorbed at different rates by the different types of tissue cells (e.g., malignant vs. healthy). More specifically, the contrast agent may be a compound that has different uptake rates for healthy and malignant tissue. During treatment, the presence of the contrast agent in the plasma effluent may then be used to identify the presence of any cancerous cells.

According to one embodiment of the present disclosure, a medical device for treating and analyzing tissue is disclosed. The device includes a plasma applicator having a housing. The housing includes a substantially tubular shape and defining a lumen therethrough. The lumen is in fluid communication with an ionizable media source configured to supply ionizable media thereto. The applicator also includes one or more electrodes adapted to couple to the housing. The electrodes are coupled to a power source that energizes the electrodes to ignite the ionizable media to form a plasma plume for treating tissue. The device also includes an effluent-collection attachment coupled to the plasma applicator, the effluent-collection attachment configured to collect at least a portion of a plasma effluent.

A method for treatment and analysis of tissue is also contemplated by the present disclosure. The method includes the steps of generating and supplying a plasma plume to the tissue through a plasma applicator to form a plasma effluent and collecting at least a portion of the plasma effluent through an effluent-collection attachment. The method also includes the steps of analyzing at least the portion of the plasma effluent with a spectrometer to generate plasma plume data and processing the plasma plume data to determine at least one of type of tissue and effectiveness of energy delivery to the tissue.

Another method for treatment and analysis of tissue is contemplated by the present disclosure. The method includes the steps of generating and supplying a plasma plume to the tissue having malignant and normal cells through a plasma applicator to form a plasma effluent and collecting at least a portion of the plasma effluent through an effluent-collection attachment. The method also includes the steps of analyzing at least the portion of the plasma effluent with a spectrometer to generate plasma plume data, processing the plasma plume data to determine a ratio of malignant to normal tissue and outputting the ratio and determining progression of malignant tissue based on the ratio and terminating generation and supply of the plasma plume based on the progression.

BRIEF DESCRIPTION OF THE DRAWINGS

The accompanying drawings, which are incorporated in and constitute a part of this specification, illustrate exemplary embodiments of the disclosure and, together with a general description of the disclosure given above, and the detailed description of the embodiments given below, serve to explain the principles of the disclosure, wherein.

DETAILED DESCRIPTION

Plasmas are generated using electrical energy that is delivered as either direct current (DC) electricity or alternating current (AC) electricity at frequencies from about 0.1 hertz (Hz) to about 100 gigahertz (GHz), including radio frequency ("RF", from about 0.1 MHz to about 100 MHz) and microwave ("MW", from about 0.1 GHz to about 100 GHz) bands, using appropriate generators, electrodes, and antennas. Choice of excitation frequency, the workpiece, as well as the electrical circuit that is used to deliver electrical energy to the circuit affects many properties and requirements of the plasma. The performance of the plasma chemical generation, the delivery system and the design of the electrical excitation circuitry are interrelated, i.e., as the choices of operating voltage, frequency and current levels (as well as phase) effect the electron temperature and electron density. Further, choices of electrical excitation and plasma applicator hardware also determine how a given plasma system responds dynamically to the introduction of new ingredients to the host plasma gas or liquid media. The corresponding dynamic adjustment of the electrical drive, such as dynamic match networks or adjustments to voltage, current, or excitation frequency are required to maintain controlled power transfer from the electrical circuit to the plasma.

Figure 1:
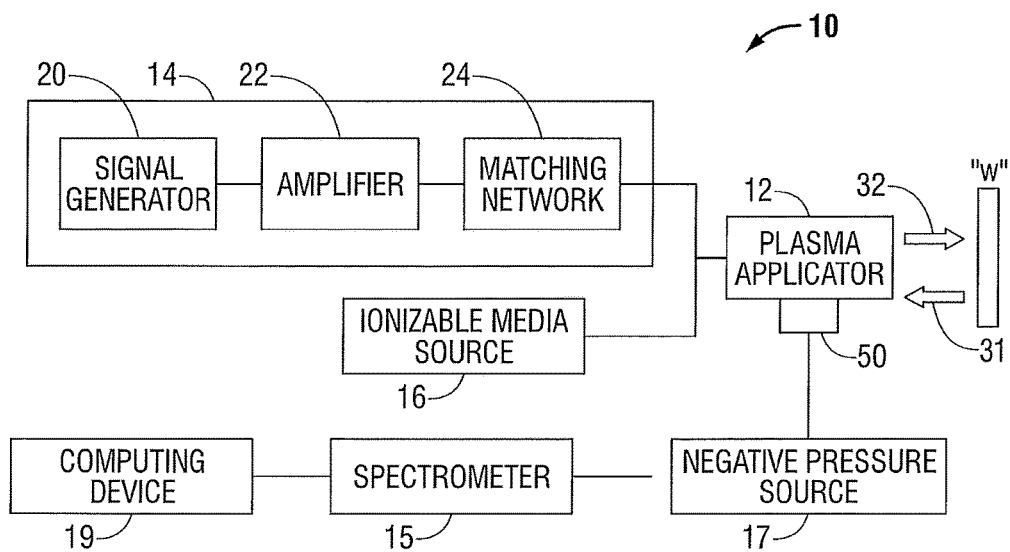
FIG. 1 is a schematic diagram of a plasma system according to the present disclosure.

Referring initially to FIG. 1, a plasma system 10 is disclosed. The system 10 includes a plasma applicator 12 that is coupled to a power source 14 and an ionizable media source 16. Power source 14 includes any required components for delivering power or matching impedance to plasma applicator 12. More particularly, the power source 14 may be any radio frequency generator or other suitable power source capable of producing power to ignite the ionizable media to generate plasma. The plasma applicator 12 may be utilized as an electrosurgical pencil for application of plasma to tissue and the power source 14 may be an electrosurgical generator that is adapted to supply the device 12 with electrical power at a frequency from about 0.1 MHz to about 1,000 MHz and, in another embodiment, from about 1 MHz to about 13.6 MHz. The plasma may also be ignited by using continuous or pulsed direct current (DC) electrical energy.

Power source 14 includes a signal generator 20 coupled to an amplifier 22. The signal generator 20 outputs a plurality of control signals to the amplifier 22 reflective of the desired waveform. The signal generator 20 allows for control of desired waveform parameters (e.g., frequency, duty cycle, amplitude, etc.). The amplifier 22 outputs the desired waveform at a frequency from about 0.1 MHz to about 1,000 MHz and in another illustrative embodiment from about 1 MHz to about 13.6 MHz. The power source 14 also includes a matching network 24 coupled to the amplifier 22. The matching network 24 may include one or more reactive and/or capacitive components that are configured to match the impedance of the load (e.g., plasma plume) to the power source 14 by switching the components or by frequency tuning.

The system 10 provides a flow of plasma through the device 12 to a workpiece "W" (e.g., tissue). Plasma feedstocks, which include ionizable media (FIG. 2), are supplied by the ionizable media source 16 to the plasma applicator 12. During operation, the ionizable media is provided to the plasma applicator 12 where the plasma feedstocks are ignited to form plasma plume 32 containing ions, radicals, photons from the specific excited species and metastables that carry internal energy to drive desired chemical reactions in the workpiece "W" or at the surface thereof.

The ionizable media source 16 provides ionizable feedstock to the plasma applicator 12. The ionizable media source 16 may include a storage tank and a pump (not explicitly shown) that is coupled to the plasma applicator 12. The ionizable media may be a liquid or a gas such as argon, helium, neon, krypton, xenon, radon, carbon dioxide, nitrogen, hydrogen, oxygen, etc. and their mixtures, and the like, or a liquid. These and other gases may be initially in a liquid form that is gasified during application.

During use, the plasma applicator 12 is used to apply the plasma plume 32 to the tissue for coagulating, ablating, or otherwise treating tissue. When the plasma plume 32 is applied to the workpiece "W" (e.g., tissue) a plasma effluent 31 is generated that includes various compounds, particulates and other species from the treated tissue. The plasma applicator 12 includes an effluent-collection attachment 50 for collecting the species from the plasma effluent 31 for analysis.

The system 10 also includes a spectrometer 15 coupled to the effluent-collection attachment 50 to analyze the species collected from the plasma effluent 31. The system 10 may include a negative pressure source 17 to siphon the species into the effluent-collection attachment 50 and/or directly into the spectrometer 15. The negative-pressure source 17 may be a vacuum pump, fan, circulator, and the like. The spectrometer 15 may be a so-called optical sensor configured as a so-called "lab-on-chip" type device and may utilize any suitable spectroscopy technique such as laser-induced breakdown spectroscopy spark-induced breakdown spectroscopy, bio-aerosol mass spectrometry, and the like.

In embodiments, the spectromenter 15 may be a surface attracting sensor such as a spins sensor utilizing microelectromechanical technology instead of the optical sensors of the "lab-on-chip" type diagonistics. The spectrometer 15 may be coupled to a computing device 19 for analyzing the results spectroscopy analysis. The computing device 19 may include a variety of inputs and/or outputs for interfacing with the spectrometer 15 as well as any other suitable peripheral devices (e.g., keyboard, mice, monitors, printers, etc.).

Figure 2:
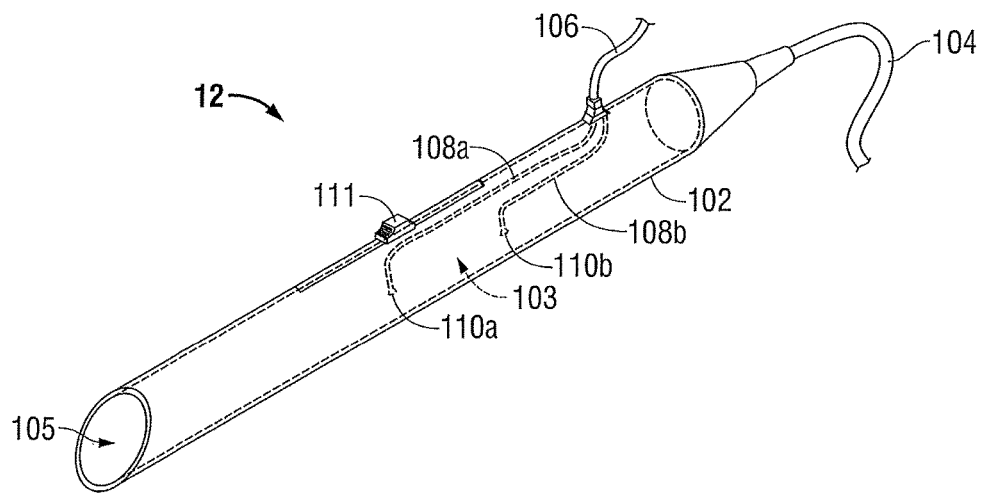
FIG. 2 is a perspective view of a plasma applicator according to one embodiment of the present disclosure.

With reference to FIG. 2, the plasma applicator 12 is shown. The plasma applicator 12 includes a housing 102, which may be formed from any suitable dielectric material. The housing 102 may have a substantially tubular shape defining a lumen 103 therethrough terminating in an opening 105 at a distal end of the housing 102. The plasma applicator 12 is coupled to the ionizable media source 16 via tubing 104 thereby coupling the lumen 103 in fluid communication with the ionizable media source 16.

The plasma applicator 12 is also coupled to the power source 14 via a cable 106. The cable 106 encloses a plurality of leads 108a and 108b connecting one or more electrodes 110a and 110b to the power source 14. The electrodes 110a and 110b may be disposed within the lumen 103, within the housing 102 or on an outer surface thereof to provide for resistive or capacitive coupling with the ionizable media being fed through the lumen 103. The electrodes 110a and 110b may be formed from any suitable conductive material and may have a variety of shapes and sizes (e.g., ring, needle, etc.).

The plasma applicator 12 includes controls 111 (e.g., toggle switch) coupled to the power source 14 and the ionizable media source 16. Upon actuation, the controls 111 regulate the flow of ionizable media from the ionizable media source 16 and the flow of power from the power source 14, such that the ionizable media flowing through the lumen 103 is ignited therein and is ejected from the opening 105 to form the plasma effluent 31.

Figure 3:
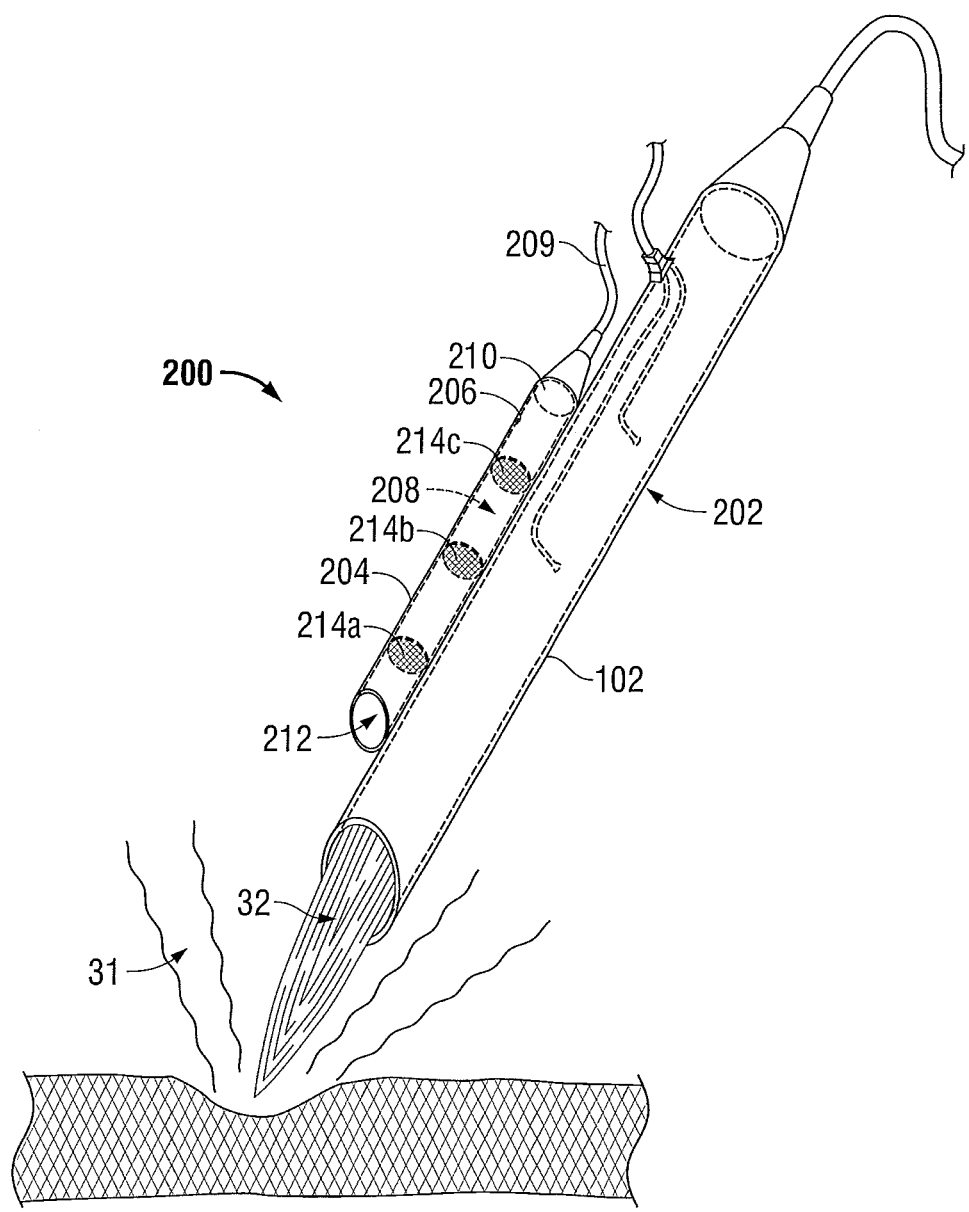
FIG. 3 is a perspective view of a plasma applicator according to another embodiment of the present disclosure.

FIG. 3 illustrates a plasma analysis device 200 that includes a plasma applicator 202 and an effluent-collection attachment 204. The plasma applicator 202 may be substantially similar to the plasma applicator 12 of FIG. 2. The effluent-collection attachment 204 includes a housing 206 which may be formed of any suitable type of heat-resistant material. The housing 206 may have a substantially tubular shape defining a lumen 208 therethrough. The effluent-collection attachment 204 is removably coupled to the plasma applicator 202, namely, the outer surface of the housing 206 is coupled to the outer surface of the housing 102. This may be accomplished by using rails, clamps, and any other suitable mechanisms.

The housing 206 also includes a proximal opening 210 and a distal opening 212 in communication with the lumen 208. The proximal opening 210 is coupled to the negative pressure source 17 via tubing 209. The tubing 209 may be formed from flexible heat-resistant tubing such as polytetrafluoroethylene ("PTFE") and the like. The negative pressure source 17 provides for a continuous flow of air and the plasma effluent 31 through the lumen 208. The negative pressure source 17 is also coupled to the spectrometer 15 allowing for passage of the species gathered from the plasma effluent 31 to the spectrometer 15.

The effluent-collection attachment 204 also includes a plurality of filters 214a, 214b, 214c. The filters 214a, 214b, 214c are of different filtration sizes and are arranged in a decreasing order of their respective sizes from the distal opening 212 to the proximal opening 210. This arrangements allows for sorting of the particulates from the plasma effluent 31 based on their size. Filtering of the particles allows for passage only of the particles of the smallest size to the spectrometer 15. The spectrometer 15 analyzes the filtered particles in real-time and provides the results to the computing device 19, which then processes the results and outputs the same in a readable format.

In addition to real-time analysis of filtered particles, the spectrometer 15 may also be used to analyze the particles attached to the filters 214a, 214b, 214c. The effluent-collection attachment 204 may be removed after application of the plasma plume 32 to the tissue to collect the particles from the filters 214a, 214b, 214c and submit the samples to analysis at the spectrometer 15.

Figure 4:
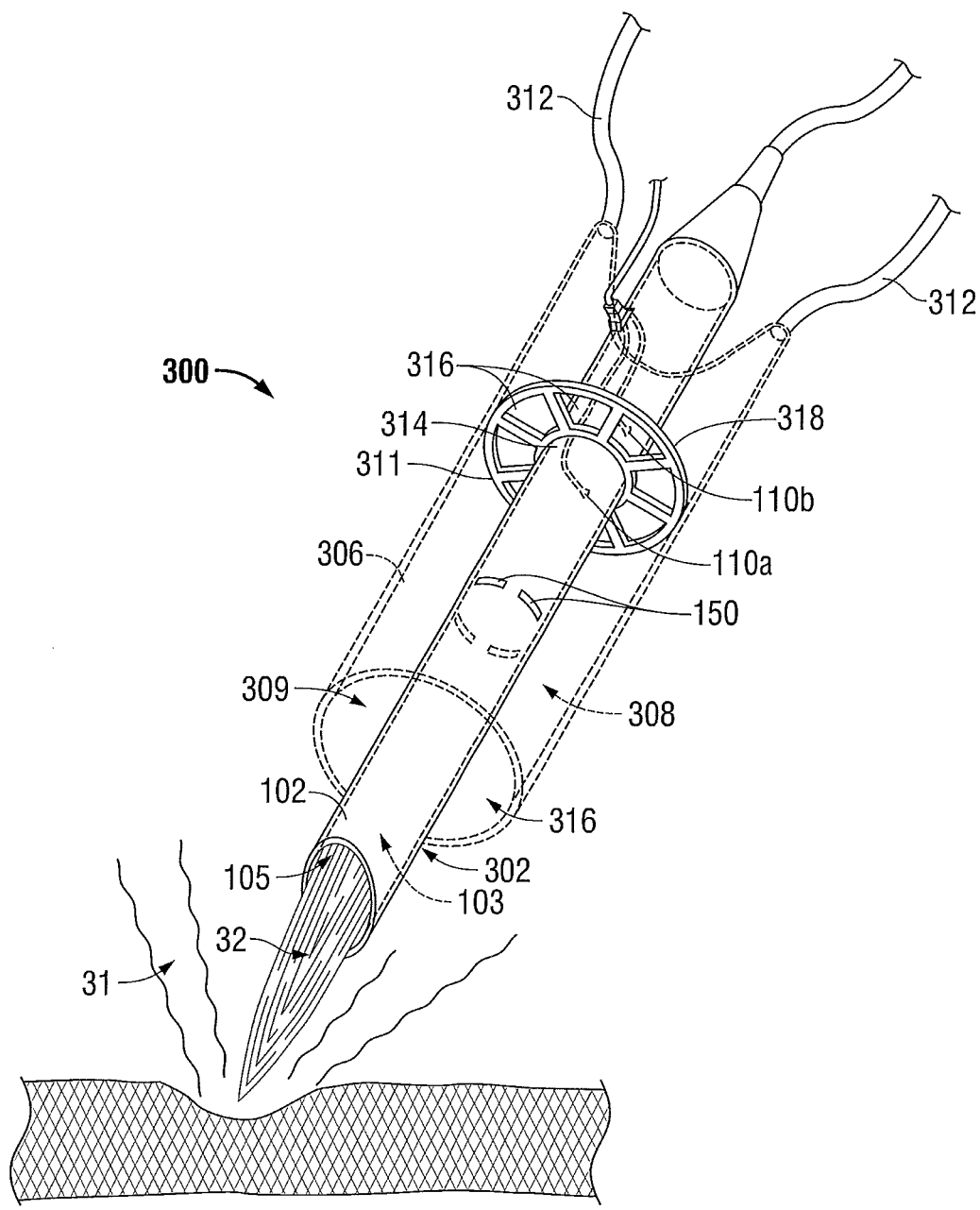
FIG. 4 is a perspective view of a plasma applicator according to another embodiment of the present disclosure.

FIG. 4 illustrates a plasma analysis device 300 that includes a plasma applicator 302 and an effluent-collection attachment 304. The plasma applicator 302 may be substantially similar to the plasma applicator 12 of FIG. 2. The effluent-collection attachment 304 is a secondary plasma applicator having a housing 306 which may be formed any suitable type of heat-resistant material and concentrically disposed about the plasma applicator 302. The housing 306 may have a substantially tubular shape defining a lumen 308 therethrough. The lumen 308 is sufficient to fit about the plasma applicator 302 and to define a secondary plasma chamber 309 between the housing 306 and the housing 102. The housing 306 may be secured to the plasma applicator 302 by a spacer 311.

The housing 306 includes a distal opening 316 and a proximal opening 318. The effluent-collection attachment 304 includes an adapter 318 coupling the proximal opening 318 to the negative pressure source 17 via tubing 312. The adapter 318 may have a funnel-type shape to couple the housing 306 to the tubing 312. In addition, the adapter 318 may couple to a plurality tubing connections.

The spacer 311 is disposed between the inner surface of the housing 306 and the outer surface of the housing 102. The spacer 311 may be disposed at any point between the housings 102 and 306 to provide for a coaxial configuration. The spacer 311 includes a central opening 314 adapted for insertion of the housing 102 therethrough and one or more flow openings 316 disposed radially around the central opening 314 to allow for the flow of plasma effluent 31 and plasma plume 32 to flow through the secondary plasma chamber 309 as discussed in more detail below. The spacer 311 may be frictionally-fitted to the housings 102 and 306 to secure the housing 306 to the housing 102. In one illustrative embodiment, the spacer 311 may be formed from a dielectric material, such as ceramic, to enhance capacitive coupling between the housings 102 and 306.

The housing 102 includes a plurality of openings 150 defined therein to couple the lumen 103 (e.g., primary plasma chamber) with the secondary plasma chamber 309. The openings 150 are disposed distally of the electrodes 110a and 110b. This configuration allows the plasma plume 32 that is generated within the lumen 103 to enter the secondary plasma chamber 309 and remain therein. In other words, the distally-directed flow of the plasma plume 32 through the opening 105 is counteracted by the negative pressure source 17, which pulls the plasma effluent 31 through the openings 150 and into the secondary plasma chamber 309. In addition, the negative pressure source 17 also pulls out the plasma plume 32 into the secondary plasma chamber 309 through the distal opening 316.

The negative pressure source 17 provides for a continuous flow of air and the plasma effluent 31 through the secondary plasma chamber 309. The negative pressure source 17 is also coupled to the spectrometer 15 allowing for passage of the species gathered from the plasma effluent 31 to the spectrometer 15. The plasma plume 32 within the secondary plasma chamber 309 performs a similar function to the filters 214a, 214b, 214c thereby breaking down larger particles for analysis by the spectrometer 15.

Figure 5:
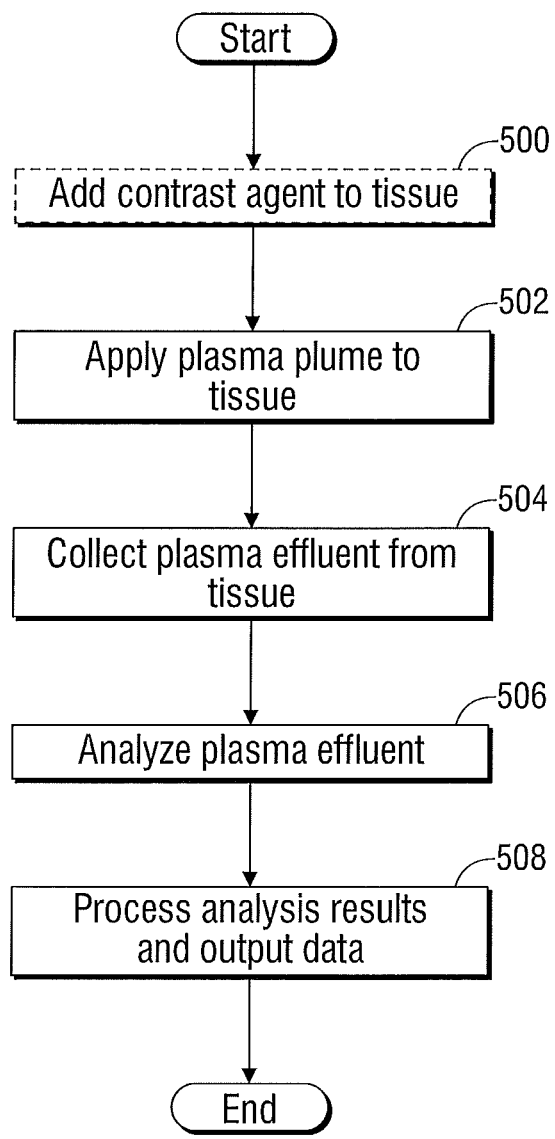
FIG. 5 is a flow chart of a method according to the present disclosure.

FIG. 5 illustrates a method of treating and analyzing tissue. To aid in the analysis of tissue, in step 500, a contrast agent may be added thereto. Step 500 is optional, based on the needs of the user. The contrast agent may be any type of substance that can be injected, ingested or otherwise provided to the patient that has different uptake rates by malignant and healthy tissues. In step 502, the plasma applicator 12 is used to generate and apply the plasma plume 32 to the tissue thereby generating the plasma effluent 31. In step 504, the plasma effluent 31 is collected by the plasma analysis device 200 or the 300, in particular, by the effluent-collection attachments 204 or 304. The negative pressure source 17 provides for the flow of the plasma effluent 31 into the effluent-collection attachments 204 or 304, which then filter (or otherwise process) the particles contained in the plasma effluent 31 prior to transporting them to the spectrometer 15.

In step 506, the spectrometer 15 analyzes the plasma effluent 31. In one embodiment, this may be done by analyzing the plasma effluent 31 for protein types and sizes. Protein types are indicative of types of tissue, and the analysis results may be processed by the computing device 19 to output the tissue type for the user. The output may be processed in real-time to provide the user with real-time biopsy results, namely, continual updates regarding the type of tissue being treated.

Protein sizes are indicative of the efficiency of energy delivery to the tissue. More specifically, the size of the protein chains is inversely proportional to the energy being delivered to the tissue (e.g., larger amounts of energy result in smaller protein chains). The filters 214a, 214b, 214c of the effluent-collection attachment 204 are used to filter the proteins to obtain the particles of desired size for analysis. In another embodiment, the effluent-collection attachment 304 is used to break down the particles from the plasma effluent 31 to the desired size.

In step 508, the computing device 19 processes the data from the spectrometer 15. The computing device 19 determines tissue type and/or progression of treatment. In one embodiment, the computing device 19 may continually update the analysis results based on the data received from the spectrometer 15. This may be particularly useful in treating cancerous tissue (e.g., skin cancer), since the computing device 19 may indicate when majority of the cancerous tissue has been removed. In another embodiment, the analysis may be done after the treatment, based on the samples collected by the filters 214a, 214b, 214c. This type of analysis is more suited for a more detailed, post-treatment determination of the type of tissue.

In one embodiment, the system and method of the present disclosure may be utilized in a Mohs procedure, which is a type of a surgical procedure for treating skin cancer. The disclosed systems and method are suitable for simultaneous resectioning and examination of the removed tissue, which is one of the main goals of the Mohs procedure.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method for treatment and analysis of tissue comprising:
   generating and supplying a plasma plume to tissue through a plasma applicator to form a plasma effluent;
   collecting a portion of the plasma effluent through an effluent-collection attachment by filtering the portion of the plasma effluent through a plurality of filters;
   analyzing the portion of the plasma effluent with a spectrometer to generate plasma plume data; and
   processing the plasma plume data to determine at least one of a type of the tissue or effectiveness of energy delivery to the tissue.

2. A method according to claim 1, further comprising:
   adding a contrast agent to the tissue, wherein the contrast agent has different uptake rates for malignant and healthy tissue.

3. A method according to claim 2, wherein processing the plasma plume data further includes determining an amount of malignant tissue based on a presence of the contrast agent in the plasma plume.

4. A method according to claim 1, wherein collecting the portion of the plasma effluent further includes passing the portion of the plasma effluent through a plasma chamber.

5. A method according to claim 1, wherein collecting the portion of the plasma effluent further includes supplying a negative pressure source to the effluent-collection attachment to provide for a flow of the portion of the plasma effluent through the effluent-collection attachment.

6. A method for treatment and analysis of tissue comprising:
   generating and supplying a plasma plume to tissue through a plasma applicator to form a plasma effluent;
   collecting a portion of the plasma effluent through an effluent-collection attachment;
   analyzing the portion of the plasma effluent with a spectrometer to generate plasma plume data; and
   processing the plasma plume data to determine at least one of a type of the tissue or effectiveness of energy delivery to the tissue by determining a ratio of malignant to normal tissue.

7. A method according to claim 6, further comprising:
   determining progression of malignant tissue based on the ratio; and
   terminating generation and supply of the plasma plume based on the determined progression.

8. A method for treatment and analysis of tissue comprising:
- generating and supplying a plasma plume to tissue having malignant and normal cells through a plasma applicator to form a plasma effluent;
- collecting a portion of the plasma effluent through an effluent-collection attachment;
- analyzing the portion of the plasma effluent with a spectrometer to generate plasma plume data;
- processing the plasma plume data to determine a ratio of malignant to normal tissue; and
- determining progression of malignant tissue based on the ratio and terminating generation and supply of the plasma plume based on the determined progression.

9. A method according to claim 8, further comprising:
- adding a contrast agent to the tissue, wherein the contrast agent has different uptake rates for malignant and healthy tissue.

10. A method according to claim 9, wherein processing the plasma plume data further includes determining an amount of malignant tissue based on a presence of the contrast agent in the plasma plume.

11. A method according to claim 8, wherein collecting the portion of the plasma effluent further includes filtering the portion of the plasma effluent through a plurality of filters.

12. A method according to claim 8, wherein collecting the portion of the plasma effluent further includes passing the portion of the plasma effluent through a plasma chamber.

13. A method according to claim 8, wherein collecting the portion of the plasma effluent further includes supplying a negative pressure source to the effluent-collection attachment to provide for a flow of the portion of the plasma effluent through the effluent-collection attachment.

* * * * *